US006358531B1

(12) United States Patent
Day et al.

(10) Patent No.: US 6,358,531 B1
(45) Date of Patent: Mar. 19, 2002

(54) METHOD FOR PREPARING POROUS SHELLS OR GELS FROM GLASS PARTICLES

(75) Inventors: Delbert E. Day; Samuel D. Conzone, both of Rolla, MO (US)

(73) Assignee: The Curators of the University of Missouri, Columbia, MI (US)

(*) Notice: Subject to any disclaimer, the term of this patent is extended or adjusted under 35 U.S.C. 154(b) by 0 days.

(21) Appl. No.: 09/241,492

(22) Filed: Feb. 1, 1999

(51) Int. Cl.[7] ............................. A61K 9/14; A61K 9/26; A61K 9/64; B01J 21/08; C03B 9/00
(52) U.S. Cl. ..................... 424/489; 424/464; 424/469; 424/478; 424/456; 65/21.3; 502/262; 544/129
(58) Field of Search ................................ 424/489, 464, 424/478, 469, 456; 65/21.3; 502/262; 544/129

(56) References Cited

U.S. PATENT DOCUMENTS

| 4,487,620 A | * 12/1984 | Neusy ........................ 65/21.3 |
| 4,789,501 A | 12/1988 | Day et al. .................... 252/645 |
| 4,889,707 A | 12/1989 | Day et al. .................... 424/1.1 |
| 5,011,677 A | 4/1991 | Day et al. .................... 424/1.1 |
| 5,011,797 A | 4/1991 | Day et al. ...................... 501/33 |
| 5,039,326 A | 8/1991 | Day et al. .................... 65/21.1 |
| 5,302,369 A | 4/1994 | Day et al. .................. 424/1.29 |
| 5,352,645 A | * 10/1994 | Schwartz ..................... 502/262 |
| 5,403,573 A | 4/1995 | Day et al. .................. 424/1.29 |
| 5,717,092 A | * 2/1998 | Armistead et al. ........... 544/129 |

OTHER PUBLICATIONS

Ansehl "Early Studies of [198]Au in the Treatment of Synovitis of the Knee" Ann. Rheum. Dis, vol. 32, (1973) Supplement pp. 1–2.

Boerbooms et al. "Radio–Synovectomy in Chronic Synovitis of the Knee Joint in Patients with Rheumatoid Arthritis" European Journal of Nuclear Medicine, vol. 10 (1985) pp. 446–449.

Davis et al. "Radiopharmaceuticals for Radiation Synovectomy: Evaluation of Two Yttrium–90 Particulate Agents" Journal of Nuclear Medicine, vol. 30, No. 6 (1989) pp. 1047–1055.

Day et al. "Radiotherapy Glasses" An Introduction to Bioceramics, Advanced Series in Ceramics, World Scientific, vol. 1 (1994) p. 305–317.

Devi et al. "Optical Properties of $Pr^{3+}$ Ions in Lithium Borate Glasses" Physics and Chemistry of Glasses, vol. 37, No. 1 (1996) pp. 36–40.

(List continued on next page.)

Primary Examiner—Thurman K. Page
Assistant Examiner—Amy E Pulliam
(74) Attorney, Agent, or Firm—Senniger, Powers, Leavitt & Roedel

(57) ABSTRACT

A method is provided for preparing shells, concentric shells or porous, homogenous gels from alkali borate glass particles at low temperatures (i.e. room temperature or less than above 100° C.). The alkali borate glass particles contain one or more cations such as aluminum which react with an aqueous solution containing an anion such as hydroxide to form an aqueous insoluble material having a solubility limit of less than about 0.01 wt. percent. The resulting shells or gels may be used in many different applications such as a filler in resins, as filters, precursors for nano-sized powders, as thin surface films or catalyst support media. The resulting shells or gels may also have a chemotherapeutic drug added thereto, following which the resulting product is administered to a mammal and the insoluble material is dissolved form the product in vivo through administration of chelating agent.

38 Claims, 12 Drawing Sheets

OTHER PUBLICATIONS

Downs et al. "Hollow Glass Microspheres by Sol–Gel Technology" Sol–Gel Technology for Thin Films, Fibers, Preforms, Electronics and Specialty Shapes, Ed. L. Klein, 330–380, Noyes Publications, NJ (1988).

Ehrhardt et al. "Investigation of Pre–Operative Sterilization of Kidney Cancers Using Intra–Arterial Samarium–153 Microspheres" Proceedings of the 39th Annual Meeting, Journal of Nuclear Medicine, No. 845 (Jun. 9–12 1992) p. 1024.

Erbe et al. "Chemical Durability of $Y_2O_3$–$Al_2O_3$–$SiO_2$ Glasses for the In Vivo Delivery of Beta Radiation" Journal of Biomedical Materials Research, vol. 27 (1993) pp. 1301–1308.

Erbe et al. "Properties of $Sm_2O_3$–$Al_2O_3$–$SiO_2$ Glasses for In Vivo Applications" Journal of American Ceramics Soc., vol. 73, No. 9 (1990) pp. 2708–2713.

Hall "The Decision to Operate in Rheumatoid Arthritis" Symposium on Rheumatoid Arthritis, Orthopedic Clinics of North America, vol. 6, No. 3 (1975) pp. 675–684.

Hendricks "Glass Spheres" Ceramics and Glasses vol. 4, Engineered Materials Handbook, ASM International, USA (1991) p. 418–422.

Houle et al. "Hepatocellular Carcinoma: Pilot Trial of Treatment with Y–90 Microspheres" Radiology, vol. 172 (1989) pp. 857–860.

Hyatt et al. "Glass Properties in the Yttria–Alumina–Silica System" Journal of the American Ceramic Society, vol. 70, No. 10 (1987) pp. C–283—C–287.

Ingrand "Characteristics of Radio–Isotopes for Intra–Articular Therapy" Ann. Rheum. Dis., vol. 32 (1973) Supplement p. 3–9.

Klein "Sol–Gel Process" Ceramics and Glasses vol. 4, Engineered Materials Handbook, ASM International, USA (1991) pp. 209–214.

Nachimuthu et al. "Influence of Cations on the Optical Properties of $Nd^{3+}$, $Eu^{3+}$ and $Er^{3+}$ Doped Borate Glasses" Physics and Chemistry of Glasses, vol. 38, No. 2 (1997) pp. 59–62.

Neves et al. "Palladium–109 and Holmium–166 Potential Radionuclides for Synoviotherapy–Radiation Absorbed Dose Calculations" Journal of Applied Radiation and Isotopes, vol. 38, No. 9 (1987) pp. 745–749.

Russell et al. "Dosimetry Calculations for Yttrium–90 Used in the Treatment of Liver Cancer" Endocurietherapy/Hyperthermia Oncology, vol. 4, No. 7 (1988) pp. 171–186.

Shoup "Sol–Gel Processes" Ceramics and Glasses vol. 4, Engineered Materials Handbook, ASM International, USA (1991) pp. 445–452.

Sledge et al. "Treatment of Rheumatoid Synovitis of the Knee with Intraarticular Injection of Dysprosium 165–Ferric Hydroxide Macroaggregates" Journal of the American Rheumatism Association, vol. 29, No. 2 (1986) pp. 153–159.

Smiley et al. "Hollow Microspheres: More than Just Fillers" Mechanical Engineering, Feb. 1986, pp. 27–30.

P. Spooren et al. "Synovectomy of the Knee with $^{90}Y$" Eur. J. Nuc. Med., vol. 10 (1985).

Taylor et al. "Synovectomy of the Knee in Rheumatoid Arthritis" Ann. Rheum. Dis. vol. 31 (1972) pp. 159–161.

Wehrenberg II, "Shedding Pounds in Plastics: Microspheres are Moving" Mechanical Engineering, Oct. 1978, pp. 58–63.

International Search Report for analogous PCT Application No. PCT/US00/02433 dated Aug. 3, 2000.

International Search Report for analogous PCT Application No. PCT/US00/02388 dated Jun. 14, 2000.

* cited by examiner

METHOD FOR PREPARING POROUS SHELLS OR GELS FROM GLASS PARTICLES

BACKGROUND OF THE INVENTION

This invention relates to a method for preparing a shell or porous gel from glass particles and, more particularly, to such a method in which glass particles are reacted, non-uniformly corroded or partially dissolved to convert solid glass particles into a product composed of shells, concentric shells or a porous, homogeneous gel which can be used in various applications.

Hollow glass microspheres have been produced in large quantities since the 1930's (C. D. Hendricks, "Glass Spheres", in Ceramics and Glasses, Vol. 4 Engineered Materials Handbook, 418–422, ASM International, USA (1991); and Neusy U.S. Pat. No. 4,487,620). Traditionally hollow glass microspheres have been processed by mixing glass forming raw materials (i.e. soda, lime and silica) with an organic material such as urea. These materials are mixed into a slurry, which is subsequently dried into a cake and crushed into small (<200 µm) particles. The particles are then introduced into a high temperature flame where the glass forming materials melt, and the gas released from decomposition of the organic material forms hollow glass microspheres. Many refinements of this general technique have been used to make the majority of hollow microspheres which are now commercially available. The main disadvantage of this method is that flame temperatures exceeding 1200° C. must be used to produce the hollow microspheres. The hollow microspheres made using this "burn out" method are primarily used as fillers in light weight polymers, high temperature insulation and as fillers in paints (C. D. Hendricks, supra; L. H. Smiley, "Hollow Microspheres: More Than Just Fillers, Mech. Eng. Feb. 27–30 (1986); and R. H. Wehrenberg, "Shedding Pounds in Plastics: Microspheres are Moving", Mech. Eng. Oct. 58–63 (1978)).

Hollow glass microspheres can also be produced using sol-gel processing (R. L. Downs et al., "Hollow Glass Microspheres by Sol-Gel Technology" in Sol-Gel Technology for Thin Films, Fibers, Preforms, Electronics and Specialty Shapes, Ed. L. Klein, 330–380, Noyes Publications, NJ, (1988); L. C. Klein, "Sol-Gel Process" in Ceramics and Glasses, Vol. 4 Engineered Materials Handbook, 209–214, ASM International, USA (1991); and R. D. Shoup, "Sol-Gel Processes", in Ceramics and Glasses, Vol. 4 Engineered Materials Handbook, 445–452, ASM International, USA (1991)). A sol is first prepared by mixing metal alkoxides, such as tetraethylorthosilicate (TEOS), with water and ethanol. This sol is then heated and acid catalyzed to form a silicate gel. The gel is dried and crushed into particles which are spheroidized in a high temperature (>1200° C.) flame. While in the flame, the gel particles melt and decomposing organic groups release gas to form hollow glass microspheres. This technique is used to prepare hollow glass microspheres with very high purity and uniform wall thicknesses. The sol gel processing of hollow glass microspheres is very costly due to the high cost of the metal alkoxides used as raw materials. Sol gel processing also requires high temperatures and multiple processing steps which must be closely monitored. Thus, this technique is only used for very specialized applications such as the formation of hollow microspheres which are impregnated with deuterium and tritium for use in laser fusion experiments (R. H. Wehrenberg, supra).

There is a continuing need for improved processes for preparing a shell or porous gel from glass particles, particularly for processes which can be carried out at low temperatures (<100° C.) and which can produce hollow, porous microspheres of many different chemical compositions.

SUMMARY OF THE INVENTION

Among the several objects of the invention may be noted the provision of a method for preparing from glass particles a product composed of a shell filled with colloidal particles or gel, concentric shells, or a porous, homogenous gel; the provision of such a method by which porous/hollow shells may be produced at or near room temperature; the provision of a method of the type described which advantageously produces a porous product which may be filled with various types of liquids and gases; the provision of such a method which allows hollow/porous products of many different chemical compositions to be prepared; and the provision of a method for administering a chemotherapeutic drug which permits porous microspheres formed by glass particle/solution reactions to be dissolved with a chelating agent. Other objects and features will be in part apparent and in part pointed out hereinafter.

Briefly, the present invention in one aspect is directed to a method for preparing a shell or porous gel from glass particles which involves the steps of:

(a) forming particles of an alkali borate glass composition containing one or more cations which react with an aqueous solution containing an anion reactive with the cation to form an aqueous insoluble material having a solubility limit of less than about 0.01 wt. percent;

(b) immersing the glass composition particles in the aforementioned aqueous solution so that the particles react and form the insoluble material which is essentially the same size as the as-made particles with the alkali and borate dissolving from the glass particles; and (c) allowing the chemical reaction to continue until the alkali and boron are substantially completely dissolved from the glass particles and the resulting product is composed of a shell filled with colloidal particles or gel, concentric shells or a porous, homogeneous gel, the product being nonradioactive and not adapted for neutron irradiation.

In another aspect, the invention is directed to a method for administering a chemotherapeutic drug which involves the three above-noted steps and the additional steps of adding a chemotherapeutic drug to the above-noted resulting product and administering the then resulting product to a mammal, and thereafter dissolving the insoluble material from this product in vivo through the administration of a chelating agent. Another additional step may involve heat treating the above-noted resulting product so as to improve its mechanical strength or to control its porosity/permeability for the purpose of controlling the rate at which a drug is released or the product may be filled with a drug.

Figure 3:
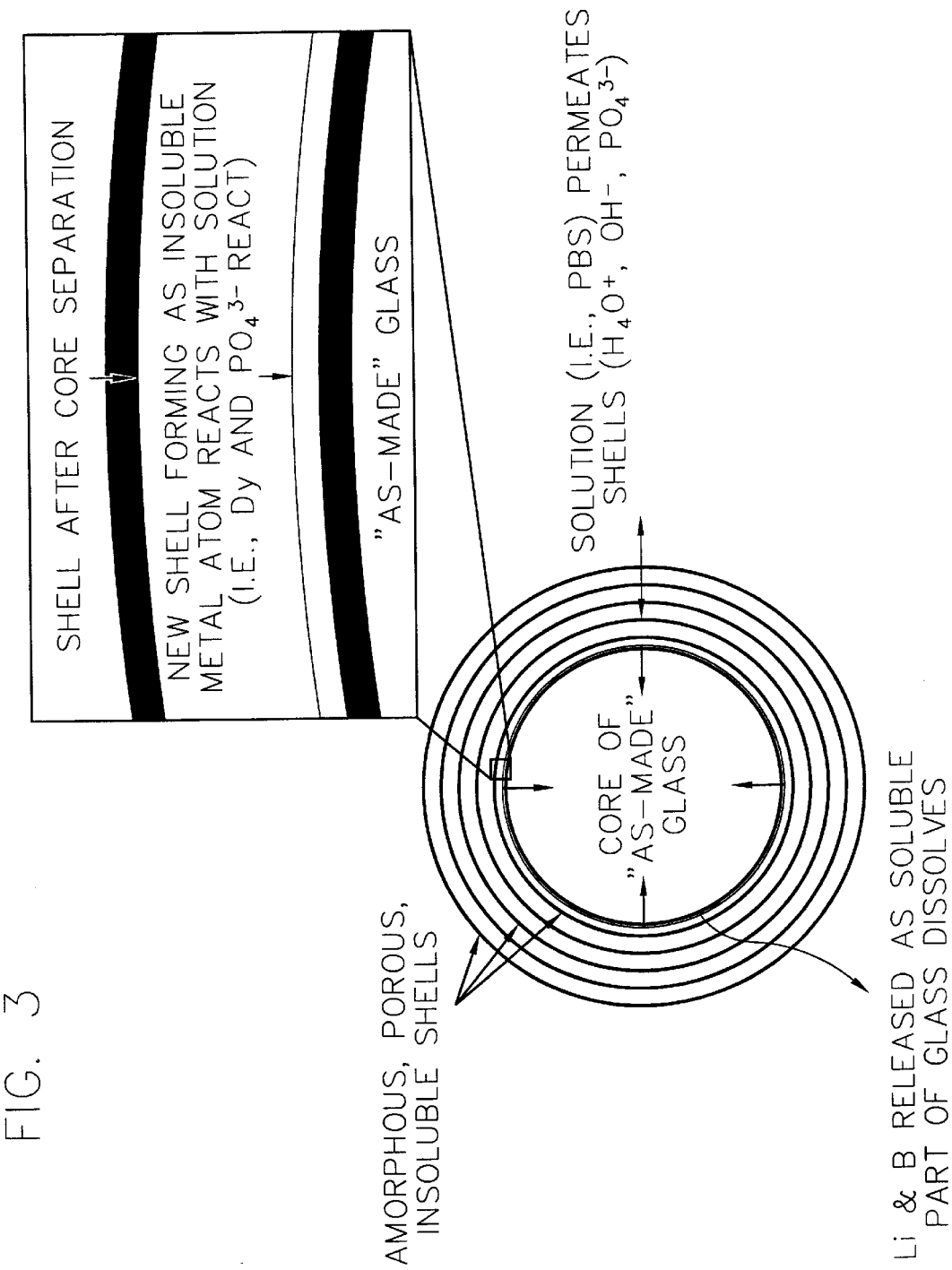
Figure 4:
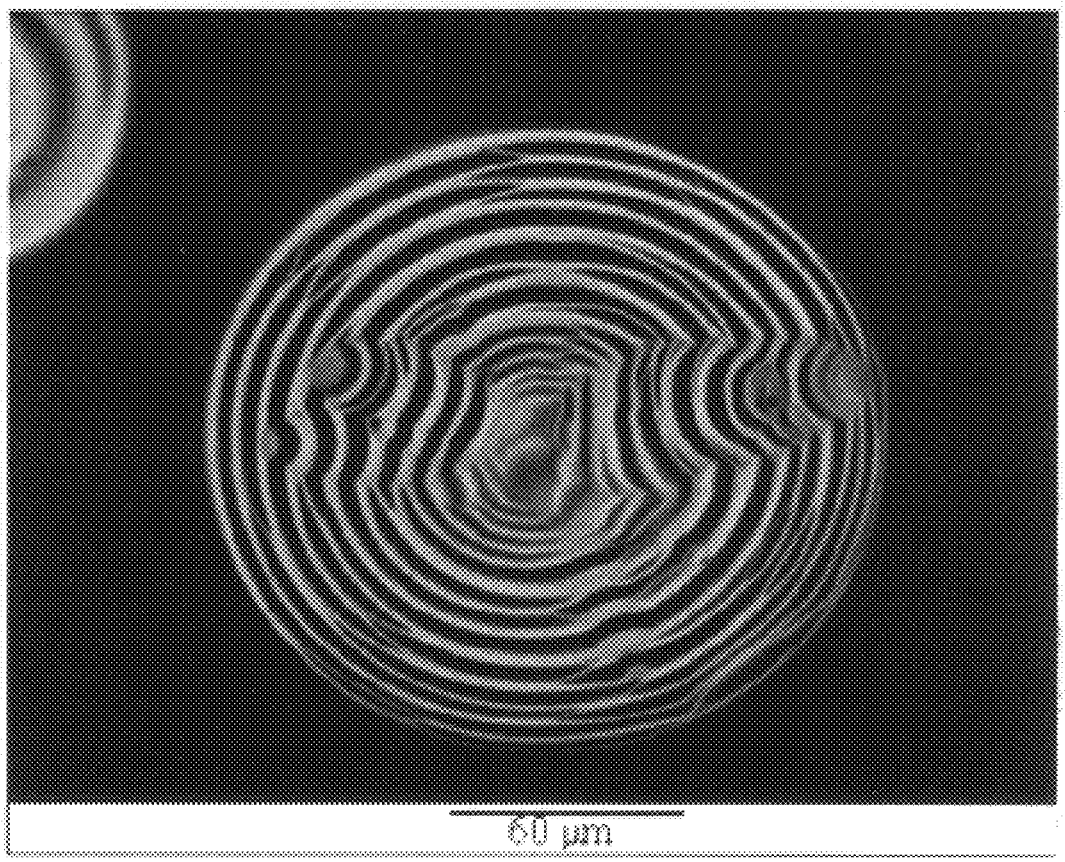
Figure 5:
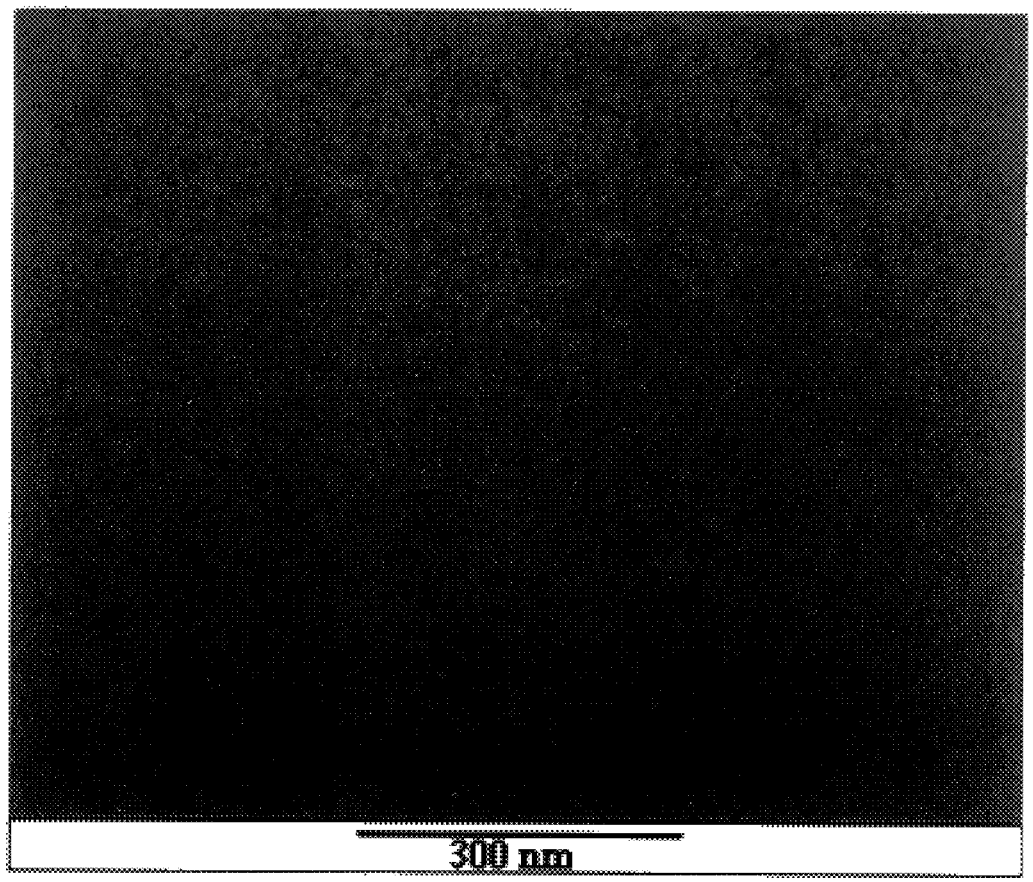
Figure 6:
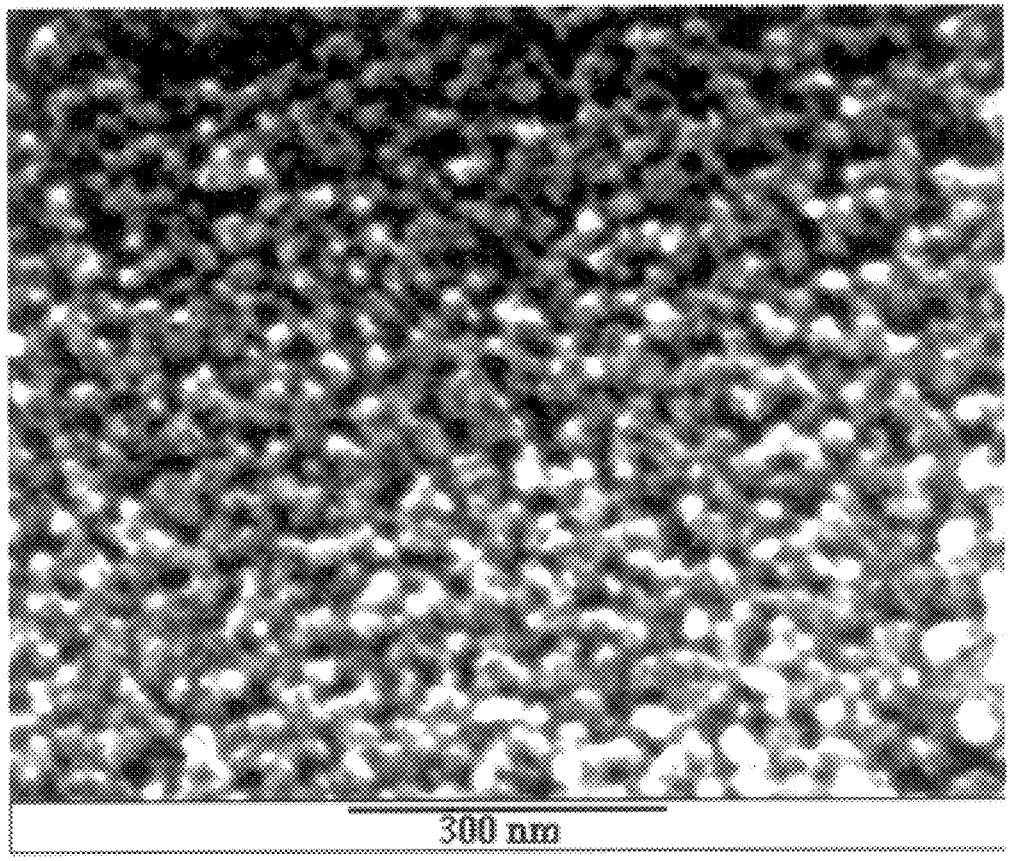
Figure 7:
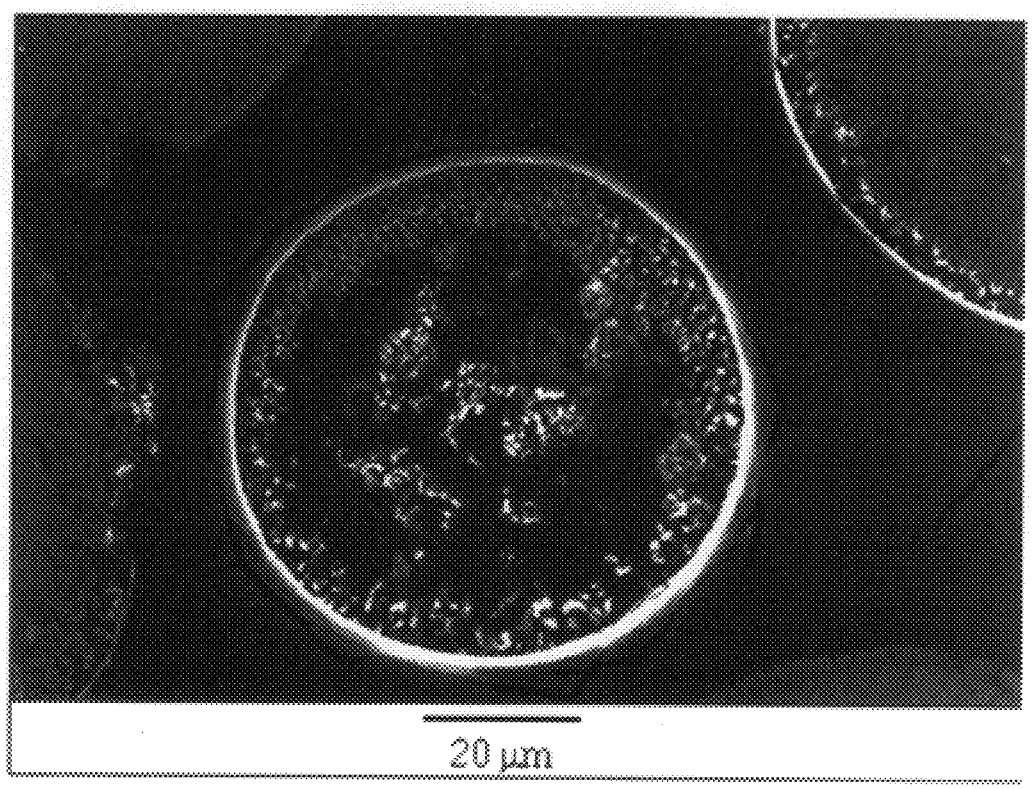
Figure 8:
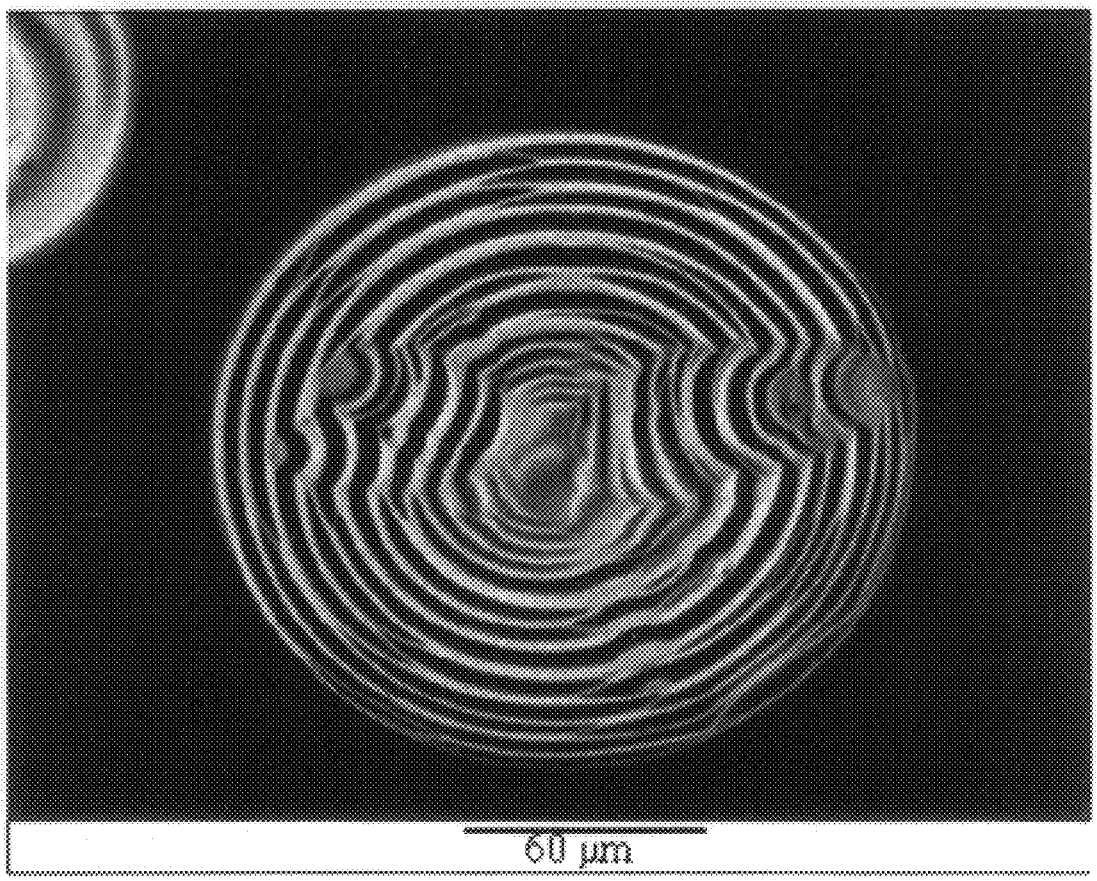
Figure 9:
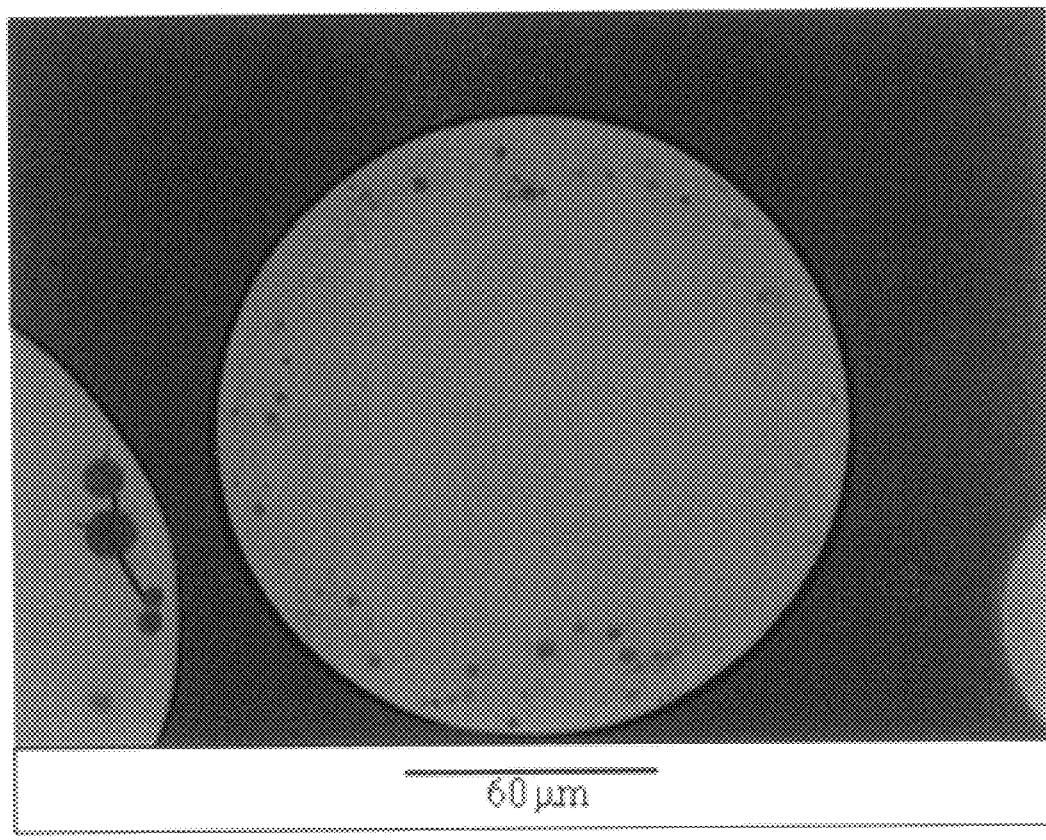
Figure 11:
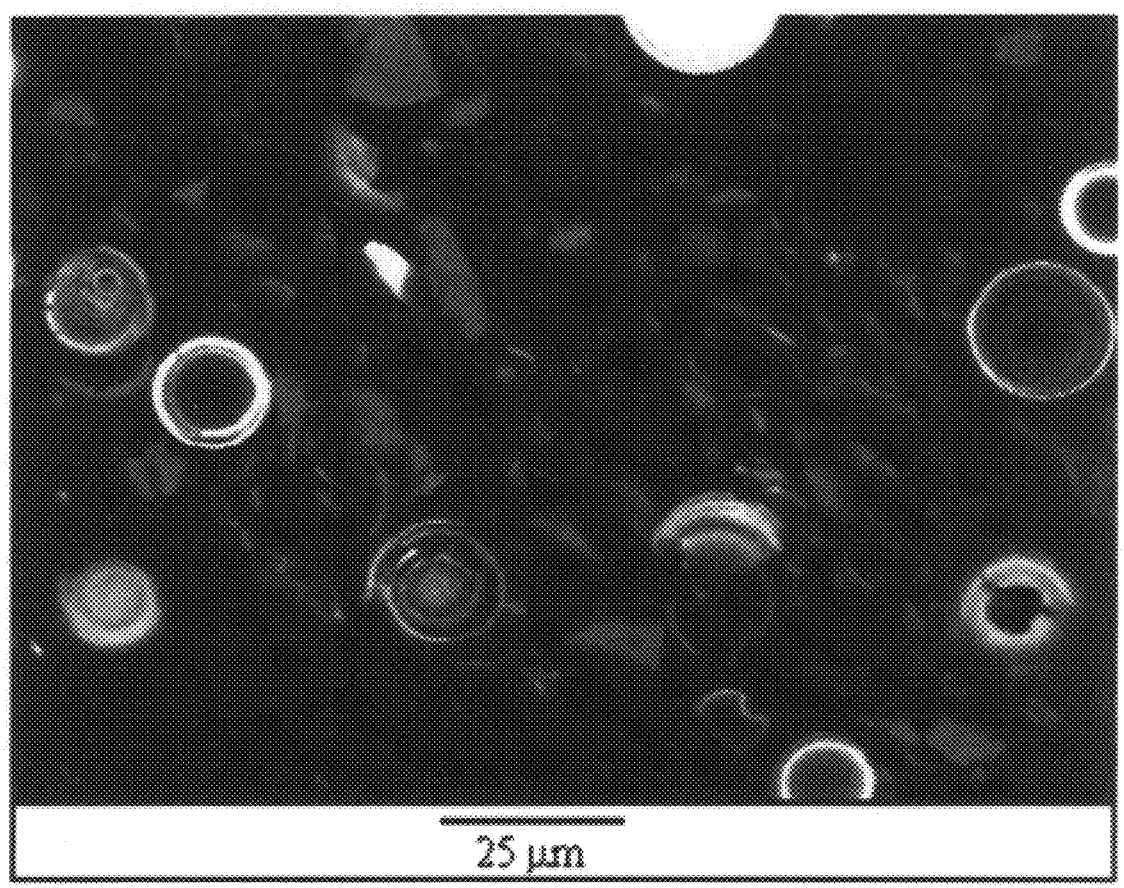
Figure 12:
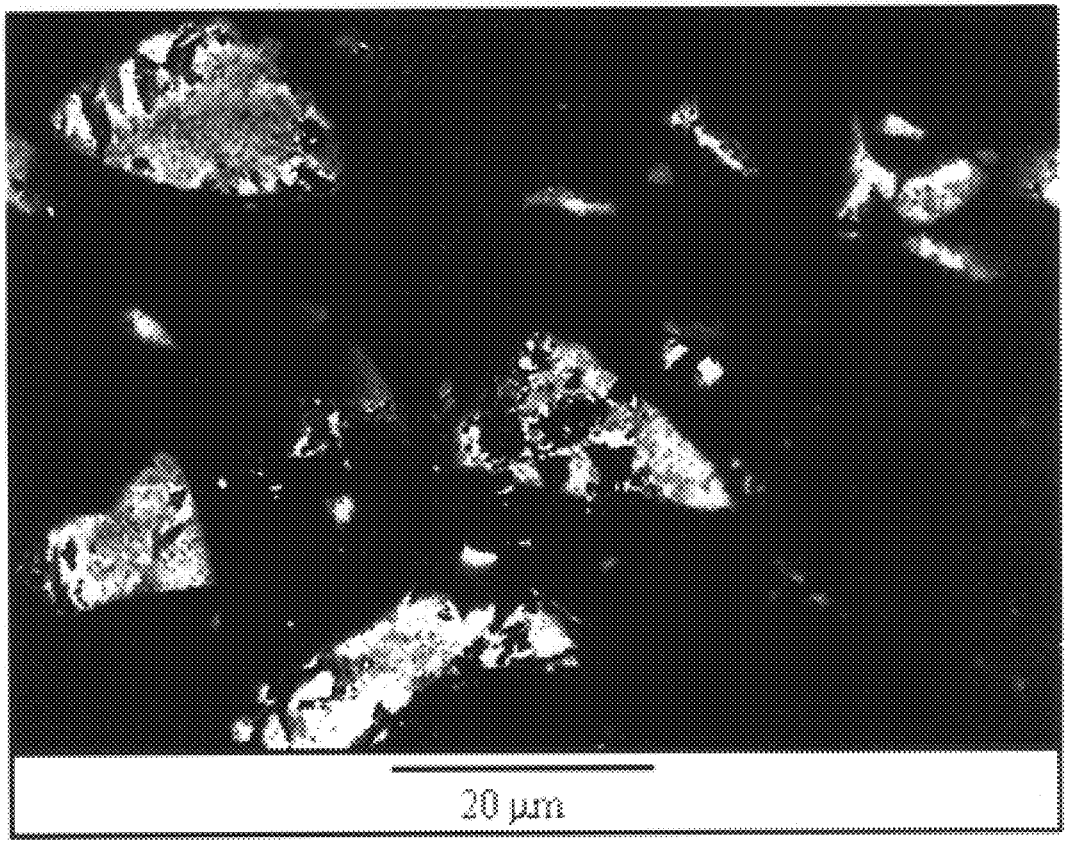

FIG. 3 is a schematic model of the chemical reaction occurring between a borate glass and a solution, such as PBS, where an insoluble material is formed as a series of concentric shells;

FIG. 4 is a cross-sectional view of a $Dy_2O_3$—$Li_2O$—$B_2O_3$ glass microsphere which has been immersed in PBS solution for 24 hours at 37° C. and then impregnated with polymethyl methacrylate. The white region is composed of an amorphous, porous dysprosium phosphate gel;

FIG. 5 is a high magnification SEM micrograph showing the smooth, external surface of an "as-made" $Dy_2O_3$—$Li_2O$—$B_2O_3$ glass microsphere;

FIG. 6 is a high magnification SEM micrograph showing the surface of a $Dy_2O_3$—$Li_2O$—$B_2O_3$ glass microsphere which was immersed in PBS solution for 24 hours at 37° C.;

FIG. 7 is a backscatter SEM image of a cross-sectioned $Dy_2O_3$—$Li_2O$—$B_2O_3$ microsphere which initially contained 3 wt. % $Dy_2O_3$, and was fully reacted with PBS solution at 37° C.;

FIG. 8 is a backscatter SEM image of a cross-sectioned $Dy_2O_3$—$Li_2O$—$B_2O_3$ glass microsphere which initially contained 10 wt. % $Dy_2O_3$, and was fully reacted with PBS solution at 37° C.;

FIG. 9 is a backscatter SEM image of a cross-sectioned $Dy_2O_3$—$Li_2O$—$B_2O_3$ glass microsphere which initially contained 30 wt. % $Dy_2O_3$, and was fully reacted with PBS solution at 37° C.;

FIG. 10 shows optical micrographs of $Dy_2O_3$—$Li_2O$—$B_2O_3$ glass microspheres and borosilicate glass particles immersed in PBS solution at 37° C. (A, B and C). At 1 hr:42 minutes, 25 $\mu$l of 0.75M EDTA solution was added and complete chelation (dissolution) of the spherical dysprosium phase was observed at 2 hr:05 minutes (E and F). The bottom micrographs D, E and F show the disappearance of the shells after the addition of EDTA, but the angular, irregular borosilicate glass particles remain unaffected;

FIG. 11 is a backscatter SEM micrograph of $Dy_2O_3$—$Li_2O$—$B_2O_3$ microspheres which have reacted in the rat to form dysprosium phosphate and borosilicate glass particles (irregular shape) after two weeks in a rat knee. The rat knee did not receive an EDTA injection so the insoluble dysprosium phosphate microspheres are still present along with the insoluble borosilicate particles; and FIG. 12 is a backscatter SEM micrograph of irregular borosilicate glass particles remaining in a rat knee after the addition of EDTA. Note that all microspheres have been completely dissolved by the EDTA and none are visually detectable.

DESCRIPTION OF THE PREFERRED EMBODIMENTS

Figure 1:
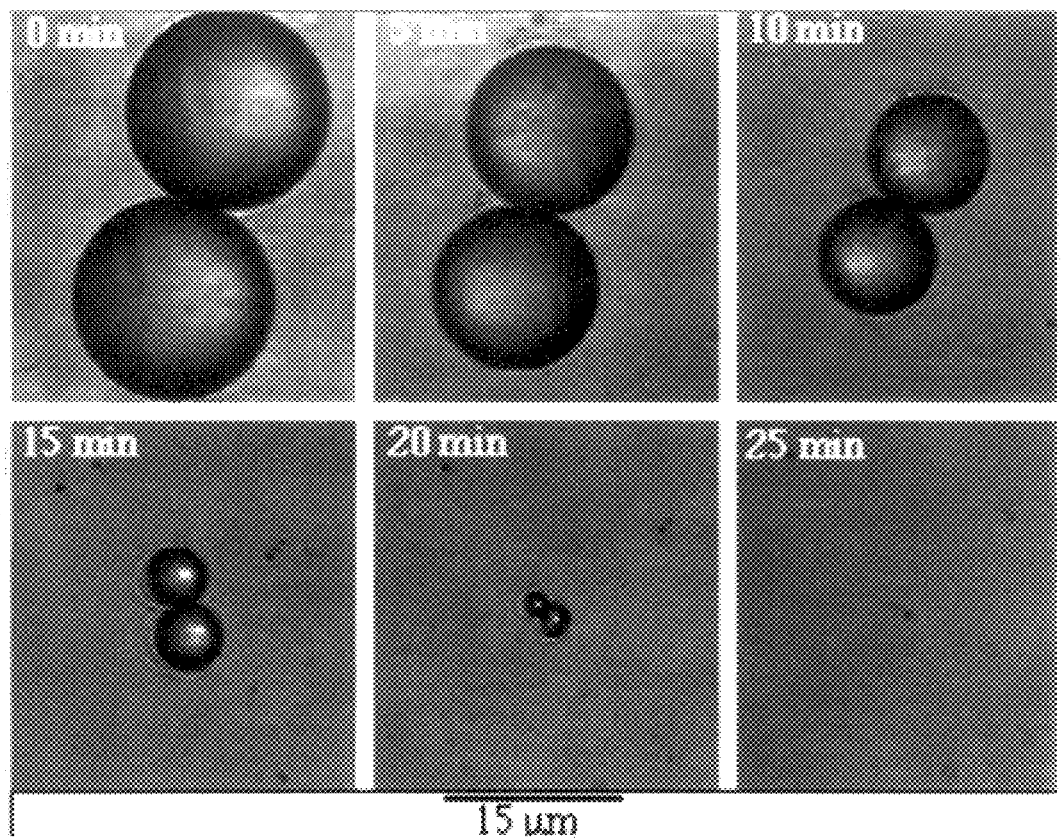
FIG. 1 shows optical micrographs of pure $Li_2O_3$—$B_2O_3$ glass microspheres immersed in a phosphate buffered saline (PBS) solution at 37° C. for 0, 5, 10, 15, 20 and 25 minutes with the microspheres progressively shrinking in size as they uniformly dissolve in the solution.

In accordance with the present invention, it has now been found that hollow/porous shells may be produced from glass particles by a method which can be carried out at or near room temperature. The novel method of the invention employs alkali borate glasses of an appropriate composition which are first crushed into particles or made into spheres of the desired size. Pure alkali borate glasses have very poor chemical durability and will completely dissolve when immersed in aqueous solutions as shown in FIG. 1. In accordance with the invention, the alkali borate glass compositions utilized contain a cation such as a rare earth ($Dy^{3+}$), calcium or iron ($Ca^{2+}$ or $Fe^{3+}$) which react with an aqueous solution containing an anion such as hydroxide or phosphate to form an aqueous insoluble material having a solubility limit of less than about 0.01 wt. %. When the alkali borate glass composition particles are immersed in an aqueous solution, such as a body fluid for example, non-uniform reaction, corrosion or dissolution of the glass particles occurs and the reaction between the cation in the glass composition and the anion in the aqueous solution forms an insoluble material which is essentially the same size and shape as the "as-made" particles, see FIG. 2.

FIG. 3 shows a schematic representation of the mechanisms which occur during the non-uniform reaction of the alkali borate glass compositions. As shown, during the chemical reaction, the alkali and boron ions dissolve from the glass particles or microspheres and go into solution. The insoluble cations in the glass (e.g. $Ca^{2+}$, $Dy^{3+}$) react with $OH^-$ and/or $PO_4^{4-}$ anions present in the aqueous solution (e.g. saline solution or body fluid) to form an insoluble oxide, hydroxide or phosphate gel on or around the microspheres or glass particles. In one aspect of the invention, this insoluble gel initially forms at the original surface of the "as-made" particles or microspheres. Thus, the gel remains the same shape and size as the "as-made" particles or microspheres. As the non-uniform reaction progresses inward, toward the center of the microsphere, the dissolving core can separate from the outer shell depending upon the content of the reacting cation in the glass and the rate at which the glass reacts with the solution. As this core detachment occurs, another shell can begin to form around the separated core as it continues to react non-uniformly. These shell formation and disconnection or detachment steps continue to occur until the inner core of "as-made" glass has completely reacted. The resulting reaction product is generally composed of concentric shells of an amorphous, or crystalline highly porous solid.

By varying the amount of insoluble cation present in the glass composition used for the glass/aqueous solution reaction, one can obtain resulting products having one of three different microstructures as shown in FIGS. 7–9. The microstructures shown in FIGS. 7–9 are based primarily upon SEM investigations performed on dysprosium lithium borate ($Dy_2O_3$—$LiO_2$—$B_2O_3$) glass microspheres which were reacted in phosphate buffered saline (PBS) solution. FIG. 7 shows the first microstructure characterized by a rigid dysprosium phosphate shell filled with colloidal particles of the same composition obtained by reacting a glass composition containing 3 wt. % $Dy_2O_3$ with PBS solution at 37° C.

FIG. 8 shows the second type of microstructure previously discussed above which can be described as a concentric shell microstructure formed by reacting an "as-made" dysprosium lithium borate glass containing 10 wt. % $Dy_2O_3$ with PBS solution at 37° C.

FIG. 9 shows the third type of microstructure formed by the glass/aqueous solution reaction depicted in FIG. 3 and can be described as a porous, homogenous gel formed by reacting an "as-made" dysprosium lithium borate glass containing 30 wt. % $Dy_2O_3$ with PBS solution at 37° C. Because the glass contained such a high amount of insoluble dysprosium, a continuous gel formed during the glass/aqueous solution reaction.

In the practice of the invention, the alkali borate glass employed may contain lithium, sodium, potassium, rubidium or cesium individually or a mixture of these alkalis. The cation contained in the alkali borate glass composition may be an alkaline earth metal cation such as calcium, magnesium, strontium or barium, a transition metal cation such as chromium or zirconium (i.e. $Cr^{3+}$ and $Zr^{4+}$), rare earth metal cation such as dysprosium, samarium, yttrium or holmium (i.e. $Dy^{3+}$, $Sm^{3+}$, $Y^{3+}$ and $Ho^{3+}$) or an aluminum ($Al^{3+}$) or iron ($Fe^{3+}$) cation. The anion or ligand contained in the aqueous solution reacted with the glass composition may be hydroxide, oxygen, phosphate, sulfate, chromate, carbonate or other anion and hydrated forms thereof which will react with the cation in the glass composition to form an aqueous insoluble material having a solubility limit of less than about 0.01 wt. %. The insoluble material may be an oxide, hydroxide, phosphate, sulfate, chromate, carbonate or hydrated form thereof. For example, when the aqueous solution is a body fluid containing phosphate anions, the insoluble material formed by chemical reaction of these anions with cations such as calcium or aluminum would be calcium or aluminum phosphate.

In the three microstructures of the products produced through the method of the present invention, the micrographs of FIGS. 7–9 are low magnification and do not show the existence of nanometer-size porosity which the dysprosium phosphate insoluble material in each microstructure possesses. Such porosity is advantageous in the use of such materials as filtration or drug delivery devices where porosity is essential.

The method of the present invention through the achievement of non-uniform reaction of alkali borate glass compositions provides a number of advantages. An important and practical advantage is that the method may be performed at low temperatures (i.e. room temperature or <100° C.). While the microspheres employed for aqueous reaction are produced using a high temperature flame, the method of the invention for preparing the porous/hollow shells is performed at or near room temperature. Room temperature processing allows porous/hollow shells to be produced and then filled with substances which will not tolerate high temperatures. These microspheres or glass compositions can be reacted as described and then filled with drug solutions or organic materials useful for treating ailments and diseases within the body. Thus, low temperature processing of porous/hollow shells constitutes a major advantage over the currently available high temperature methods described above when the glass compositions are intended to be filled with substances that cannot withstand temperatures above about 100° C.

Another advantage of the method of the invention is that it can be used to produce hollow microspheres which are also porous and hence easily fillable with various types of liquids, solids and gases. Microspheres produced by the burn-out and sol gel techniques previously described do not have porous walls and are difficult to fill with any substance.

Still another major advantage of the novel method of the invention is that many different chemical compositions of hollow microspheres can readily be produced. The composition of the porous/hollow shells is determined by whatever insoluble cations are incorporated into the "as-made" glass and by the anions in the solution. As mentioned above, such cations may be rare earth metal cations, alkaline earth metal cations, transition metal cations (like iron), aluminum or actinide cations incorporated into alkali borate glasses to produce hollow/porous microspheres. Thus, the method of the invention provides a major advantage over the high temperature burn-out and sol gel methods since the latter only allow hollow microspheres to be formed from glass forming constituents. With these two methods shells are only oxides, but with the present invention shells can be a phosphate, hydroxide, sulfate, chromate, etc. compound.

The three known microstructures which can be produced by the method of the present invention are shown as a shell filled with colloidal particles or gel (FIG. 7), concentric shells (FIG. 8) or a porous, homogeneous gel (FIG. 9), these microstructures being obtained by varying the amount of insoluble cation in the "as-made" glass composition utilized for the glass/aqueous solution reaction. The products of the method of the invention may be in the form of microspheres, irregularly shaped particles or an assemblage of microspheres or irregularly shaped particles and may be filled with a liquid, gas or solid material. Particles ranging in size from about 5 microns to larger than 1,000 microns can be converted into porous gels. In addition, the product produced through the practice of the invention may be further heat treated at an elevated temperature to modify the properties (e.g. strength, porosity, permeability of the shell/gel).

The products of the method of the invention may be found useful in many different applications. Thus, the resulting heat treated product may be used as a filler in resins, polymers or metals to reduce weight and enhance strength or in paints to vary the rheology of the paint. Biodegradable, hollow/porous shells produced through the invention may be impregnated with chemotherapeutic drugs, such as methotrexate, doxorubicin, alpha, beta and gamma interferons, alpha and beta tumor necrosis factors, antibiotics or other known chemotherapeutic agents, and injected into malignant tissue to slowly deliver long term doses of medication. Porous/hollow shells produced by the novel method of the invention and composed of refractory oxides, such as aluminum oxide ($Al_2O_3$), could be sintered to form high purity, high temperature insulation. Porous/hollow shells containing calcium and phosphorous could be used in vivo to accelerate the growth of bone within the body or to function as bone repair agents. Other uses for the products of the invention include use as catalyst supports where refractoriness and high porosity would be beneficial and as laser fusion targets, the porous/hollow shells being filled with deuterium and tritium and used as targets for laser fusion. Still further, the porous shells/gels produced by the method of the invention may be used as filters, precursors for nano sized powders, as thin surface films or to remove hazardous species such as chromates, arsenates, uranates and the like from solution. Another application for the products of the method of the invention is for catalyst support media, i.e. the porous shells can be impregnated internally or coated on their surface with catalytic materials. Thus, the porous, hollow shells may be impregnated throughout their thickness with metals such as platinum, palladium or the like having catalytic properties. In each instance, the product of the invention is nonradioactive and not adapted for neutron irradiation.

In another aspect of the invention, a method is provided for administering a chemotherapeutic drug to a mammal which involves the steps described above for forming a primary product of the invention, followed by the steps of adding a chemotherapeutic drug to the product, administering the resulting product to a mammal and thereafter dissolving the insoluble material from the product in vivo through the administration of a chelating agent. As previously noted, the primary product of the method of the invention is a porous material which is insoluble in solutions with a near-neutral pH such as most body fluids. Such a porous product is ideally suited for use in drug delivery since the high concentration of nano-sized porosity allows the microspheres or gels to carry a relatively large amount of a drug to a treatment area within the body for slow release of the drug. For example, porous calcium phosphate microspheres made in accordance with the method of the invention as previously described are highly suitable for drug delivery because they are chemically similar to hard tissue in the body and biocompatible. Such porous microspheres can be produced by reacting alkali-calcium-borate glass microspheres with phosphate buffered saline (PBS) solution and the resulting porous microspheres may be filled with a drug, such as an antibacterial agent, and injected into the body to treat an infected area. While such porous microspheres are thus highly suitable for drug delivery in this manner, a potential complication lies in the removal of these microspheres from the body after drug delivery therefrom has been completed.

In accordance with another aspect of the present invention, it has been found that hollow/porous microspheres may be removed from a living organism after drug delivery therefrom has been accomplished through the administration of a chelating agent. For this purpose, various chelating agents known in the art may be employed including, but not limited to, ethylenediaminetetraacetic acid (EDTA), diethylenetriaminepentaacetic acid (DTPA), nitrilotriacetic acid (NTA), trimethylenediaminetetraacetic acid, triethylenetetraaminehexaacetic acid, 1, 4, 7, 10 tetraacetic acid and hydroxyethylethylenediaminetriacetic acid (HEDTA). It will be understood that other chelating agents known to the art may also be employed in the practice of this method for dissolving or chelating the insoluble material from the microspheres after drug delivery has been achieved.

As shown by the experimental results set forth hereinafter and by reference to FIGS. 10–12, the chelating agent ethylenediaminetetraacetic acid (EDTA) was effective in dissolving porous dysprosium and calcium phosphate microspheres produced by alkali borate glass/aqueous solution reaction in vitro and dissolving dysprosium phosphate in vivo. Thus, in the in vitro chelation tests, calcium lithium borate or dysprosium lithium borate glass microspheres were placed in PBS solution at 37° C. and allowed to completely react to form calcium phosphate or dysprosium phosphate microspheres. In the in vivo tests, the knees of several Sprague Dawley rats were injected with equal weights of dysprosium lithium borate microspheres and a borosilicate glass control. In both the in vitro and in vivo tests, the administration of ethylenediaminetetraacetic acid was effective in dissolving or removing the calcium or dysprosium phosphate materials.

The following examples illustrate the practice of the invention.

EXAMPLE 1

Glass microspheres were prepared by first mixing 45 g of a lithium borate glass frit (12.5 wt. % $Li_2O$, 87.5 wt. % $B_2O_3$) with 5 g of the metal oxides $Dy_2O_3$, $Sm_2O_3$, $Y_2O_3$, $Ho_2O_3$, $Al_2O_3$, $Fe_2O_3$ and CaO, respectively. The mixed powders were then placed in a platinum crucible, melted at 1100° C. for 15 minutes, and then cast onto a stainless steel plate. The quenched glass was crushed by mortar and pestle and introduced into a propane air flame to form microspheres 5 to 15 μm in diameter. Visual inspection of the microspheres during aqueous corrosion was facilitated by their spherical shape and small size.

As shown in FIG. 1, pure lithium borate ($Li_2O$—$B_2O_3$) glass microspheres chemically reacted in a uniform manner and become progressively smaller when immersed in phosphate buffered saline solution (PBS) having the following composition at 37° C.:

| Inorganic Electrolyte | Concentration mM |
| --- | --- |
| $Na^+$ | 153.1 |
| $K^+$ | 4.2 |
| $Cl^-$ | 139.6 |
| $PO_4^{-3}$ | 9.6 |

Figure 2:
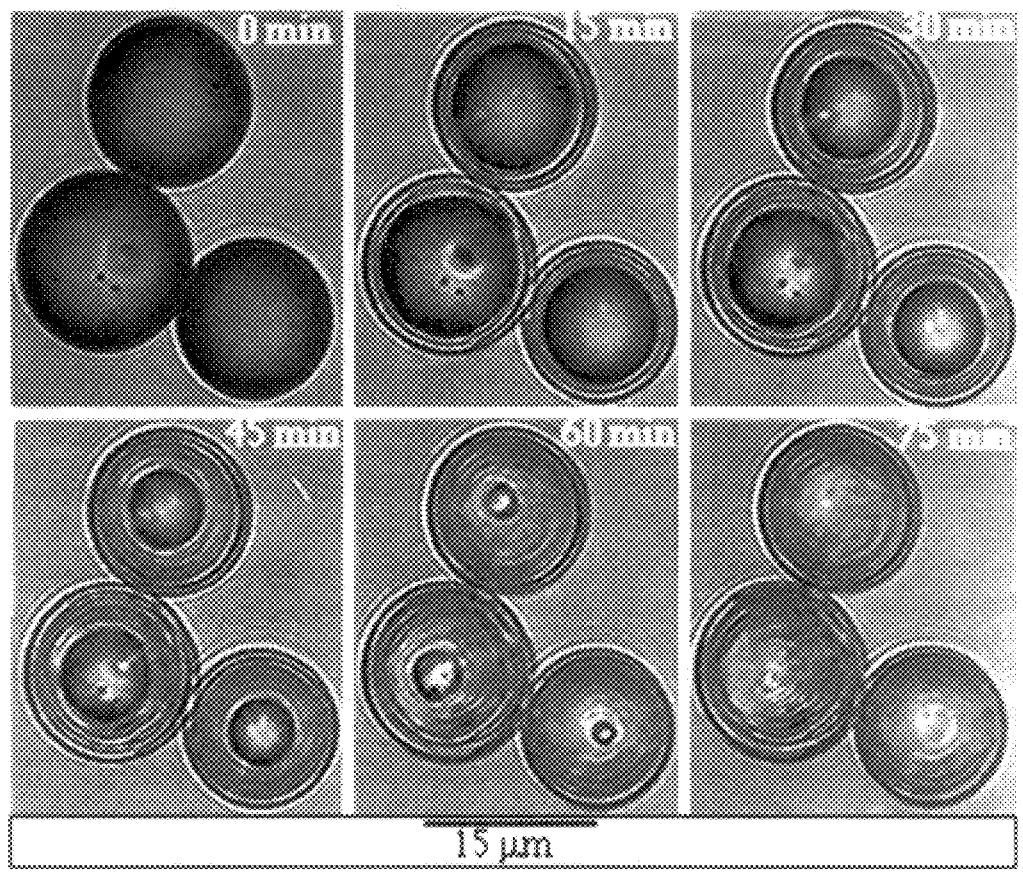
FIG. 2 shows optical micrographs of three $Dy_2O_3$—$Li_2O$—$B_2O_3$ glass microspheres immersed in PBS solution at 37° C. for 0, 15, 30, 45, 60 and 75 minutes. A spherical core of the "as-made" glass is clearly visible after 15 minutes and the core becomes progressively smaller until it is no longer detectable after 75 minutes.

However, each of the glass compositions with 10 wt. % of the metal oxides $Dy_2O_3$, $Sm_2O_3$, $Y_2O_3$, $Ho_2O_3$, $Al_2O_3$, $Fe_2O_3$ and CaO incorporated into a lithium borate glass as described above reacted non-uniformly when immersed in PBS solution at 37° C. FIG. 2 shows real time video microscopy (RTVM) optical micrographs of three $Dy_2O_3$—$Li_2O$—$B_2O_3$ glass microspheres chemically reacting non-uniformly in PBS solution at times ranging from 0 to 75 minutes. As shown, a spherical core of "as-made" glass is clearly visible after 15 minutes. Rather than dissolving uniformly and becoming progressively smaller, a shell forms at the original surface of the glass microsphere and a core of "as made" glass continues to react until it has completely reacted leaving a spherical corrosion product behind.

A reaction rate was calculated for each glass composition prepared as described above by measuring the shrinkage in the core radius as a function of time from optical micrographs obtained using RTVM. The non-uniform reaction rates calculated for each glass immersed in PBS solution at 37° C. are given in the following table and vary between 6 and 11 μm/h:

| Metal Oxide Incorporated Into the $Li_2O$—$B_2O_3$ Glass* | Reaction Rate (μm/h)** |
| --- | --- |
| $Dy_2O_3$ | 6 |
| $Sm_2O_3$ | 10 |
| $Y_2O_3$ | 6 |
| $Ho_2O_3$ | 11 |
| $Al_2O_3$ | 11 |
| $Fe_2O_3$ | 10 |
| CaO | 7 |

*10 wt. % metal oxide added to a 11.25 wt. % $Li_2O$, 78.75 wt. % $B_2O_3$ glass
**Rate at which the core of "as-made" glass radially shrinks during non-uniform reaction.

These reaction rates are high enough to completely react 15μm microspheres in PBS solution at 37° C. within 2 hours.

The mechanisms which occur during non-uniform reaction are shown in FIG. 3. Non-uniform reaction is initiated at the original surface of each glass microsphere, as lithium and boron dissolve into the surrounding solution. The insoluble cations in the glass (i.e. $Dy^{3+}$) are not completely dissolved into solution. Rather, these cations react with $OH^-$ and/or $PO_4^{3-}$ anions present in the aqueous solution adjacent to the reacting glass to form an insoluble, amorphous, gel-like shell at the surface of each glass microsphere. As time elapses, continued alkali and boron dissolution can cause the core of "as-made" glass to shrink, and separate from the outer shell. If core separation occurs, another shell will begin to form around the detached glass core as the insoluble cations again react with ions in the aqueous solution. These core separation and shell formation steps continue to occur until the core of "as-made" glass has completely reacted.

This non-uniform reaction generally results in the formation of porous/hollow shells which remain the same size and shape as the "as-made" microspheres. The reacted microspheres are generally composed of concentric shells of a porous hydroxide or phosphate gel. If, for example, a $Dy_2O_3$—$Li_2O$—$B_2O_3$ glass microsphere is reacted in PBS solution, the reacted microspheres will be composed of concentric shells of an amorphous dysprosium phosphate gel. If there is no phosphorous present in the solution (i.e. saline solution), the reacted microspheres will be composed of concentric shells of an amorphous dysprosium hydroxide gel.

EXAMPLE 2

Large (100 to 200 μm in diameter) $Dy_2O_3$—$Li_2O$—$B_2O_3$ microspheres were reacted in PBS solution at 37° C. to investigate the internal microstructure of microspheres which were non-uniformly reacted. The large $Dy_2O_3$—$Li_2O$—$B_2O_3$ glass microspheres were immersed in PBS solution for 24 hours at 37° C., dehydrated with ethanol and then impregnated with poly-methyl methacrylate. These polymer-impregnated microspheres were then cross-sectioned with a diamond saw, polished and examined by SEM. FIG. 4 shows the cross section of a $Dy_2O_3$—$Li_2O$—$B_2O_3$ microsphere after non-uniform reaction in PBS solution. The concentric shells of dysprosium phosphate are easily seen in FIG. 4. Although a concentric shell microstructure is generally produced using this technique, completely hollow microspheres may be produced by decreasing the wt. % of the insoluble metal oxide in the "as-made" microspheres, or by reacting the "as-made" microspheres in acidic or basic solutions.

High resolution SEM was used to analyze the pore structure of the large reacted microspheres. FIGS. 5 and 6 show high magnification SEM micrographs of "as-made" and reacted (PBS) $Dy_2O_3$—$Li_2O$—$B_2O_3$ glass surfaces, respectively. The "as-made" surface is smooth and dense, while the reacted surface is porous and rough with pore radii approximately 35 nm in diameter. These high resolution SEM micrographs establish that the concentric shells formed during non-uniform reaction are porous.

EXAMPLE 3

Microspheres 5 to 15 μm in diameter were placed in polycarbonate filter packets and allowed to react in PBS solution at 37° C. for time intervals ranging from 0.25 to 64 days. After each time interval, the packets were removed from the PBS solution and the weight loss was determined. Only $Dy_2O_3$—$Li_2O$—$B_2O_3$ glasses were analyzed using this weight loss technique, and these glasses lost 75% of their original weight in less than six hours. After reacting 6 hours in PBS solution, no further weight loss occurred. Thus, reaction in aqueous solutions can be used to convert the solid glass microspheres into highly porous shells in short periods of time.

EXAMPLE 4

Nitrogen absorption surface area analysis was performed on "as-made" microspheres and microspheres which were immersed in PBS solution for 24 hours at 37° C. and then air dried. The specific surface area (SSA) of $Dy_2O_3$—$Li_2O$—$B_2O_3$ microspheres increased by over 1000 times after being immersed in PBS solution at 37° C. for 24 hours. This huge increase in SSA provides further proof that the concentric shells formed during non-uniform reaction are porous.

EXAMPLE 5

Three known microstructures can be produced by the glass/solution reaction method of the present invention. These microstructures are obtained by varying the amount of insoluble cation in the "as-made" glass used for glass/solution reaction. The microstructures may also be varied by varying the amount of anion in the solution. FIGS. 7–9 show three microstructures obtained by reacting the respective glass with PBS solution, dehydrating the microspheres with ethanol, monomer infiltrating with methyl methacrylate monomer (MMA) and subsequently polymerizing (PMMA) before viewing by backscatter SEM.

The first microstructure shown in FIG. 7 is characterized by a rigid dysprosium phosphate shell filled with colloidal particles of the same composition. This microstructure was obtained by reacting a glass containing 3 wt. % $Dy_2O_3$ with PBS solution at 37° C. FIG. 7 shows a cross sectional view of a reacted dysprosium-lithium borate microsphere which initially contained 3 wt. % $Dy_2O_3$. There is a 95% weight loss associated with the formation of this shell-type microstructure.

The second type of microstructure is shown in FIG. 8 and can be described as a concentric shell microstructure. This microstructure was formed by reacting an "as-made" dysprosium-lithium borate glass which contained 10 wt. % $Dy_2O_3$ with PBS solution. An 80% weight loss is associated with the formation of this microstructure from the "as-made" glass.

The third microstructure formed by glass/solution reaction is shown in FIG. 9 and can be described as a porous, homogeneous gel. The "as-made" dysprosium-lithium borate glass used to make this microstructure initially contained 30 wt. % $Dy_2O_3$. A continuous porous, homogeneous gel formed during glass/solution reaction because the glass contained such a high amount of insoluble dysprosium. A 60% weight loss is associated with the formation of this microstructure from the "as-made" glass. While the microstructure shown in FIG. 9 appears as though it is composed of a solid microsphere, it is actually porous on the 30 to 50 nm level which is advantageous in the use of these microstructure materials as filtration or drug delivery devices where porosity would be essential.

EXAMPLE 6

The following i vitro and in vivo chelation experiments were performed to determine whether the porous microspheres formed by glass/solution reaction could be dissolved with a chelating agent such as ethylenediaminetetraacetic acid (EDTA).

The in vitro EDTA chelation tests were performed by placing either calcium-lithium borate or dysprosium-lithium borate glass microspheres in PBS solution at 37° C. and allowing them to completely react to form a calcium phosphate or dysprosium phosphate. After porous calcium phosphate or dysprosium phosphate microspheres were formed, a small amount (25 μl of 0.75M EDTA solution) was added to dissolve the particles.

Figure 10A:
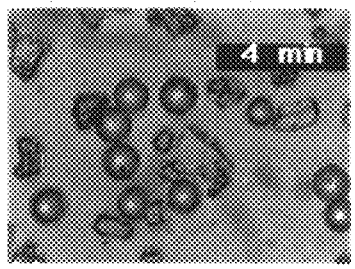
Figure 10B:
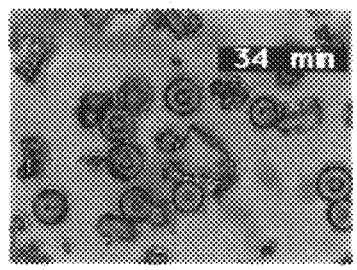
Figure 10C:
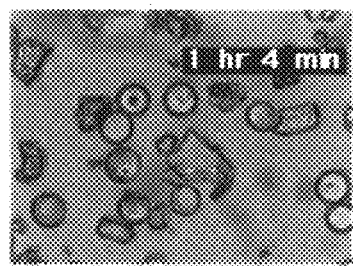
Figure 10D:
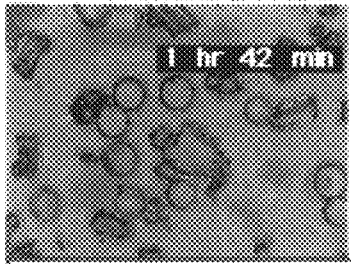
Figure 10E:
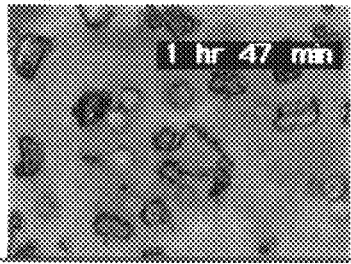
Figure 10F:
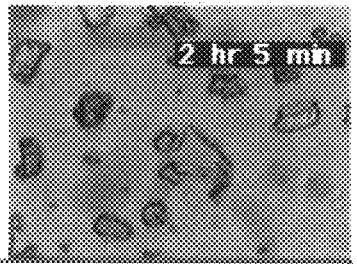

The EDTA chelation was effective in completely dissolving the hollow calcium and dysprosium phosphate materials in vitro. FIG. 10 shows micrographs from an in vitro EDTA chelation test performed on dysprosium-lithium borate glass microspheres. The top three micrographs show the dysprosium-lithium borate glass microspheres reacting with the PBS solution to form shells of a porous dysprosium phosphate. Note the appearance of a reaction layer in micrograph 10B which moves inward (10C) until the entire sphere has reacted (10D). The irregularly shaped particles in each micrograph of FIG. 10 are borosilicate glass particles (Pyrex™) which are used as inert markers since they are not dissolved by EDTA. These particles were added to act as a comparative control material. EDTA was added prior to the fourth micrograph (10D) (1 hr., 42 minutes into the test), and the microspheres were completely dissolved within 25 minutes (FIG. 10F). Thus, FIGS. 10D–10F show the disappearance of the dysprosium phosphate shells after the EDTA was added at 1 hr., 42 minutes, but the irregularly-shaped borosilicate glass particles which do not react with EDTA remain unaffected after the addition of EDTA.

Similar results were obtained with calcium-lithium borate microspheres thus demonstrating that EDTA is effective in dissolving the porous materials produced by glass/solution reaction in vitro.

For an in vivo experiment, the knees of several Sprague Dawley rats were injected with approximately 1.0 mg of an equivolumetric ratio of "as-made" dysprosium-lithium borate microspheres and irregularly-shaped borosilicate glass particles. The borosilicate particles were used as a control, since they are unaffected by EDTA. One day after injection, half of the knees were injected with 25 µl of 0.75M EDTA solution, while the other half were not injected with EDTA. All rats were then sacrificed approximately two weeks after receiving the initial injection of microspheres and borosilicate particles.. All knees were excised, dehydrated, monomer infiltrated with methyl methacrylate monomer (MMA) and polymerized (PMMA).

The polymerized knees were sectioned and examined by SEM to determine whether EDTA was effective in removing the microspheres from the knees. FIG. 11 is a micrograph showing the knee of a rat which was injected with a mixture of "as-made" glass microspheres and borosilicate glass particles without receiving an EDTA injection. During the two week period the "as-made" micropheres were in the rat, they reacted with the body fluids to form insoluble dysprosium phosphate. Since the knee was not injected with EDTA, the insoluble reacted microspheres are still present along with the insoluble borosilicate glass particles. In contrast, FIG. 12 is a SEM micrograph showing the knee of a rat that was also injected with the same mixture of "as-made" glass microspheres and borosilicate glass particles that was used for the rat in FIG. 11, but was also injected with EDTA. As shown, all of the reacted microspheres were dissolved from the knee by the EDTA in FIG. 12 and only the irregularly-shaped borosilicate glass particles remain. This in vivo test thus confirmed the results of the in vitro test showing that the EDTA chelating agent is effective in dissolving the porous microspheres produced by glass/solution reaction within the body.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A method for preparing a shell or porous gel from glass particles which comprises the steps of:
    (a) forming particles of an alkali borate glass composition containing one or more cations which react with an aqueous solution containing an anion reactive with said cation to form an aqueous insoluble material having a solubility limit of less than about 0.01 wt. %;
    (b) immersing said glass composition particles in said aqueous solution to cause reaction of said particles to form said insoluble material which is essentially the same size as the as-made particles with the alkali and boron dissolving from the glass particles; and
    (c) allowing said reaction to continue until said alkali and boron are substantially completely dissolved from said glass particles and the resulting product is composed of a shell filled with colloidal particles or gel, concentric shells or a porous, homogenous gel, said product being nonradioactive and not adapted for neutron irradiation.

2. A method as set forth in claim 1 wherein said alkali is lithium.

3. A method as set forth in claim 1 wherein said alkali is sodium.

4. A method as set forth in claim 1 wherein said alkali is potassium.

5. A method as set forth in claim 1 wherein said alkali is rubidium.

6. A method as set forth in claim 1 wherein said alkali is cesium.

7. A method as set forth in claim 1 wherein said alkali is constituted by a mixture of alkalis.

8. A method as set forth in claim 1 wherein said insoluble material is selected from the group consisting of oxides, hydroxides, phosphates, sulfates, chromates, carbonates and hydrated forms thereof.

9. A method as set forth in claim 8 wherein said insoluble material is an oxide.

10. A method as set forth in claim 8 wherein said insoluble material is a phosphate.

11. A method as set forth in claim 1 wherein said cation is selected from the group consisting of alkaline earth metal cations, transition metal cations, rare earth cations, aluminum and actinides.

12. A method as set forth in claim 11 wherein said alkaline earth metal cation is selected from the group consisting of magnesium, calcium, strontium and barium.

13. A method as set forth in claim 11 wherein said cation is aluminum.

14. A method as set forth in claim 11 wherein said cation is iron.

15. A method as set forth in claim 1 wherein said anion or ligand is selected from the group consisting of hydroxide, oxygen, phosphate, sulfate, chromate, carbonate and hydrated forms thereof.

16. A method as set forth in claim 15 wherein said anion is hydroxide.

17. A method as set forth in claim 15 wherein said anion is oxygen.

18. A method as set forth in claim 15 wherein said anion is phosphate.

19. A method as set forth in claim 1 wherein said product is in the form of microspheres, irregularly shaped particles or an assemblage of microspheres or irregularly shaped particles.

20. A method as set forth in claim 1 wherein said steps are carried out at a temperature below approximately 100° C.

21. A method as set forth in claim 20 wherein said temperature is room temperature or a temperature of 37√ C.

22. A method as set forth in claim 1 wherein said product produced in step (c) is filled with a liquid, gas or solid material.

23. A method as set forth in claim 22 wherein said filler material is a chemotherapeutic drug.

24. A method as set forth in claim 1 wherein said product produced in step (c) is dried and heat treated at an elevated temperature.

25. A method as set forth in claim 24 wherein the resulting heat treated product is added to paints, resins, polymers or metals.

26. A method as set forth in claim 24 wherein the resulting heat treated product is administered to a mammal as a bone growth or repair agent.

27. A method as set forth in claim 24 wherein said resulting heat treated product is added to a solution to remove therefrom a hazardous species selected from the group consisting of chromates, arsenates and uranates.

28. A method as set forth in claim 24 wherein said resulting heat treated product is impregnated internally or coated on its surface with catalytic material.

29. A method for administering a chemotherapeutic drug which comprises the steps of
   (a) forming particles of an alkali borate glass composition containing a cation which reacts with an aqueous solution containing an anion reactive with said cation to form an aqueous insoluble material having a solubility limit of less than about 0.01 wt. %;
   (b) immersing said glass composition particles in said aqueous solution to cause a reaction of said particles to form said insoluble material which is essentially the same size as the as-made particles with the alkali and boron dissolving from the glass particles;
   (c) allowing said reaction to continue until said alkali and boron are substantially completely dissolved from said glass particles and the resulting product is composed of a shell filled with colloidal particles or gel, concentric shells or a porous, homogenous gel, said product being nonradioactive and not adapted for neutron irradiation;
   (d) adding a chemotherapeutic drug to said product and administering the resulting product to a mammal; and
   (e) thereafter dissolving said insoluble material from said resulting product in vivo through the administration of a chelating agent.

30. A method as set forth in claim 29 wherein said chelating agent is ethylenediaminetetracetic acid.

31. A method as set forth in claim 29 wherein said alkali is lithium.

32. A method as set forth in claim 29 wherein said alkali is sodium.

33. A method as set forth in claim 29 wherein said alkali is potassium.

34. A method as set forth in claim 29 wherein said insoluble material is selected from the group consisting of oxides, hydroxides, phosphates, sulfates, chromates, carbonates and hydrated forms thereof.

35. A method as set forth in claim 34 wherein said insoluble material is an oxide.

36. A method as set forth in claim 34 wherein said insoluble material is a phosphate.

37. A method as set forth in claim 29 wherein said product produced in step (c) is in the form of microspheres, irregularly shaped particles or an assemblage of microspheres or irregularly shaped particles.

38. A method as set forth in claim 29 wherein said steps (a), (b) and (c) are carried out at a temperature below approximately 100° C.

* * * * *

UNITED STATES PATENT AND TRADEMARK OFFICE
CERTIFICATE OF CORRECTION

PATENT NO. : 6,358,531 B1
DATED : March 19, 2002
INVENTOR(S) : Delbert E. Day and Samuel D. Conzone It is certified that error appears in the above-identified patent and that said Letters Patent is hereby corrected as shown below:

<u>Title page,</u>
Item [73], Assignee: "Columbia, MI" should read -- Columbia, MO --.

<u>Column 12,</u>

Line 56, "37 √ C." should read -- 37 ºC --.

Signed and Sealed this

Twenty-fifth Day of June, 2002

Attest:

Attesting Officer

JAMES E. ROGAN
*Director of the United States Patent and Trademark Office*